United States Patent [19]

Shigeno et al.

[11] Patent Number: 5,728,841
[45] Date of Patent: Mar. 17, 1998

[54] PROCESS FOR PREPARING 1-AMINO-1,2,3-TRIAZOLE

[75] Inventors: Kazuhiko Shigeno; Tomoyasu Ono, both of Hanno; Motoaki Tanaka, Tokorozawa; Shozo Yamada, Hanno; Tetsuji Asao, Tokorozawa, all of Japan

[73] Assignee: Taiho Pharmaceutical Co., Ltd., Tokyo, Japan

[21] Appl. No.: 637,718

[22] PCT Filed: Aug. 30, 1995

[86] PCT No.: PCT/JP95/01727

§ 371 Date: Apr. 30, 1996

§ 102(e) Date: Apr. 30, 1996

[87] PCT Pub. No.: WO96/06835

PCT Pub. Date: Mar. 7, 1996

[30] Foreign Application Priority Data

Sep. 1, 1994 [JP] Japan ................. 6-232196
Jan. 30, 1995 [JP] Japan ................. 7-033028

[51] Int. Cl.$^6$ ........................... C07D 249/04
[52] U.S. Cl. ..................................... 548/255
[58] Field of Search ............................ 548/255

[56] References Cited

FOREIGN PATENT DOCUMENTS 5-502884   5/1993   Japan.

OTHER PUBLICATIONS

Adv. in Heterocyclic. Chem., 53, 113 (1992).
Zh. Org. Khim. 28, 1320 (1992).
Ber., 42, 659 (1909).
Ber., 59B, 1742 (1926).
Tetrahedron Lett., No. 34, 3295 (1967).
Synthesis, 482 (1976).
J. Chem. Soc., Perkin Trans. I., 1 (1975).

Primary Examiner—Patricia L. Morris
Attorney, Agent, or Firm—Sughrue, Mion, Zinn, Macpeak & Seas

[57] ABSTRACT

This invention is to provide a process for preparing 1-amino-1,2,3-triazole represented by formula (III):

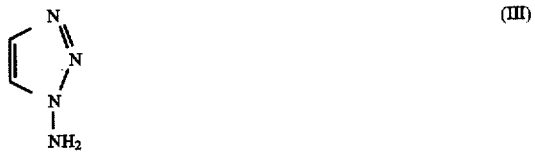

comprising cyclizing glyoxal bishydrazone represented by formula (I):

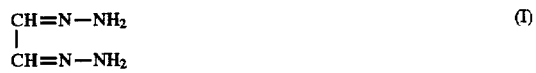

by reaction with an aqueous hydrogen peroxide solution in the presence of a catalytic amount of a transition metal oxide represented by formula (II):

$$M_mO_n$$

wherein M represents a transition metal atom; and m and n, which may be the same or different, each represent an integer of 1 to 5.

5 Claims, No Drawings

5,728,841

PROCESS FOR PREPARING 1-AMINO-1,2,3-TRIAZOLE

TECHNICAL FIELD

This invention relates to a novel process for preparing 1-amino-1,2,3-triazole which is an intermediate for producing 1,2,3-triazole, a starting material for antibiotics useful as drug.

BACKGROUND ART

Several processes for preparing N-amino-1,2,3-triazole derivatives have hitherto been known (see *Adv. in Heterocycl. Chem.*, Vol. 53, p. 113 (1992)).

These conventional techniques have their several disadvantages and are not necessarily satisfactory when applied to industrial production. For example, a process starting with 1,2,3-triazole has such problems that 1,2,3-triazole itself is expensive, and the positional selectivity of 1- or 2-amination and chemical yield in the amination are low (see *Zh. Org. Khim.*, Vol. 28, p. 1320 (1992) and Japanese Patent Publication (unexamined) No. Hei 5-502884 (International Patent Publication No. WO 92/00981)). A process starting with glyoxal bisbenzoyl-hydrazone requires two steps, and the chemical yield reached is as extremely low as not higher than 10%. Moreover, the working efficiency of the process, when applied to mass production of N-amino-1,2,3-triazole from the glyoxal bisbenzoylhydrazone, is inordinately poor (see *Ber. d. D. Chem. Gesellschaft*, Vol. 42, p. 659 (1909)).

Processes for preparing a 1-amino-1,2,3-triazole derivative represented by formula (V):

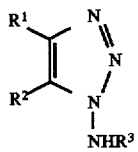

$$\text{NHR}^3 \quad (V)$$

wherein $R^1$ and $R^2$, which may be the same or different, each represent a phenyl group, a methyl group, a hydrogen atom, etc.; and $R^3$ represents a benzoyl group, a urethane derivative residue, a hydrogen atom, etc., provided that $R^1$, $R^2$ and $R^3$ are not simultaneously a hydrogen atom,
comprising oxidative cyclization of a 1,2-bishydrazone derivative represented by formula (IV):

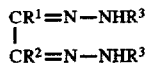

$$\begin{array}{l} CR^1=N-NHR^3 \\ | \\ CR^2=N-NHR^3 \end{array} \quad (IV)$$

wherein $R^1$, $R^2$, and $R^3$ are as defined above, are known, as disclosed in *Ber. d. D. Chem. Gesellschaft* Vol. 59B, p. 1742 (1926), *Tetrahedron Lett.*, No. 34, p. 3295 (1967), and *Synthesis*, p. 482 (1976). However, each of these processes requires an expensive or highly toxic reagent, such as activated manganese dioxide, lead tetraacetate, silver oxide or potassium ferricyanide, in excess, e.g., in an amount of 2 to 5 equivalents to the 1,2-bishydrazone derivative. Therefore, the processes not only incur increased production cost but give rise to an environmental problem in disposal of waste water. In addition, the publications have no mention of synthesis of unsubstituted 1-amino-1,2,3-triazole by ring closure of unsubstituted glyoxal bishydrazone.

An object of the present invention is to provide a process for preparing 1-amino-1,2,3-triazole on an industrial scale which is safe, easy to carry out, and economical with solving the problems caused by the conventional techniques.

Disclosure of Invention (1) The present invention relates to a process for preparing 1-amino-1,2,3-triazole represented by formula (III):

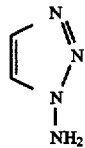

$$(III)$$

comprising cyclizing glyoxal bishydrazone represented by formula (I):

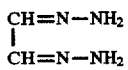

$$\begin{array}{l} CH=N-NH_2 \\ | \\ CH=N-NH_2 \end{array} \quad (I)$$

by reaction with an aqueous hydrogen peroxide solution in the presence of a catalytic amount of a transition metal oxide represented by formula (II):

$$M_mO_n$$

wherein M represents a transition metal atom; and m and n, which may be the same or different, each represent an integer of 1 to 5.

(2) The present invention also relates to a process for preparing 1-amino-1,2,3-triazole represented by formula (III) in the above process (1), which comprises cyclizing glyoxal bishydrazone represented by formula (I) by reaction with manganese dioxide.

The steps involved for the preparation of 1,2,3-triazole via 1-amino-1,2,3-triazole (III) prepared by the process of the present invention are illustrated by the following reaction scheme:

Preparation Step 1

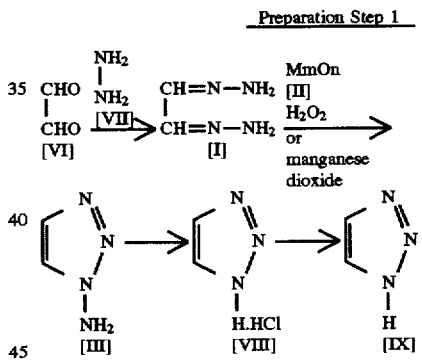

Glyoxal bishydrazone (I) which is used as a starting material in the present invention is a known compound and can be synthesized in accordance with, e.g., the process described in *Chem. Ber.*, Vol. 101, p. 1594 (1968). In some detail, glyoxal bishydrazone (I) can be obtained by reacting glyoxal (VI) or an aqueous solution thereof with hydrazine monohydrate (VII) or an aqueous solution thereof with or without a solvent. The resulting glyoxal bishydrazone (I) may be used either as prepared and isolated or after being purified.

The reaction solvent which can be used for carrying out the present invention is not particularly limited as far as it is inert to the reaction. Suitable solvents include aliphatic alcohols, such as methanol, ethanol, propanol, isopropyl alcohol, butanol, and ethylene glycol; halogenated hydrocarbons, such as chloroform, dichloromethane, and dichloroethane; aromatic hydrocarbons, such as benzene, toluene, and xylene; aliphatic hydrocarbons, such as hexane, heptane, and octane; acetic esters, such as methyl acetate and ethyl acetate; aprotic polar solvents, such as acetonitrile, N,N-dimethylformamide, N,N-dimethylacetamide, and dimethyl sulfoxide; and water. These solvents may be used either individually or as a combination thereof.

The transition metal oxide which can be used as a catalyst includes an oxide of a transition metal, e.g., tungsten, titanium, molybdenum, copper, iron, or cerium, such as tungsten (VI) oxide, titanium (IV) oxide, molybdenum (VI) oxide, copper (I) oxide, copper (II) oxide, iron (III) oxide, and cerium (IV) oxide. These transition metal oxides may be used either individually or as a combination thereof.

The transition metal oxide (II) is used in an amount of 0.001 to 1 mol, preferably 0.01 to 0.2 mol, per mole of the compound (I), and a 30% aqueous hydrogen peroxide solution is used in an amount of 0.5 to 5 mol, preferably 1 to 2 mol, per mole of the compound (I). The reaction temperature is from 0° C. up to about the boiling point of the solvent used, preferably 5° to 80° C. The reaction time is 1 to 50 hours, preferably 2 to 15 hours.

Manganese dioxide having active oxygen which can be used in the present invention preferably include activated manganese dioxide, manganese dioxide for dry cells, and manganese dioxide for ferrite. These manganese dioxides can be obtained by a known process according to prescription for laboratories, or commercially available products for use in dry cells or for production of ferrite can also be utilized as such. For example, manganese dioxide for dry cells having an effective oxygen content of not less than 91% and manganese dioxide for ferrite having an effective oxygen content of not less than 94% are produced and commercially sold by Tosoh Corporation. These manganese dioxides may be used either individually or as a mixture thereof. The term "effective oxygen content" used herein means a purity percentage of the oxygen contained as manganese dioxides per the total manganese oxides. Therefore, the manganese dioxides used in the present invention may have the above contents of trivalent manganese oxide as an impurity as well as quadrivalent manganese oxide.

The manganese dioxide is used in an amount of 1 to 5 mol, preferably 1.5 to 3 mol, per mole of the compound (I). The reaction temperature is from 0° C. up to about the boiling point of the solvent used, preferably 5° to 80° C. The reaction time is 1 to 48 hours, preferably 2 to 15 hours.

The compound obtained can easily be purified by commonly employed purification means, such as recrystallization, chromatography, and distillation. The compound can be used in the next reaction either as obtained or after purification.

1-Amino-1,2,3-triazole (III) obtained by the process of the present invention can be led to a final desired compound, 1,2,3-triazole (IX), through deamination generally known in organic chemistry in accordance with, e.g., the process described in *Ber. d. D. Chem. Gesellschaft*, Vol. 42, p. 659 (1909), *Tetrahedron Lett.*, No. 34, p. 3295 (1967), and *J. of The Chem. Soc., Perkin Trans. I*, p. 1 (1975).

BEST MODE FOR CARRYING OUT INVENTION

The present invention will now be illustrated in greater detail with reference to Reference Examples and Examples, but it should be understood that the present invention is not deemed to be limited thereto.

REFERENCE EXAMPLE 1 preparation of Glyoxal Bishydrazone (I)

In a reactor were charged a 40% aqueous solution of 1.45 g of glyoxal (VI), 1.00 g of hydrazine monohydrate, and 10 ml of water, and the mixture was stirred at room temperature for 1 hour and then at 100° C. for 3 hours. After completion of the reaction, the solvent was evaporated under reduced pressure, the residue was extracted with ethyl acetate, and the extract was dried over anhydrous sodium sulfate. The solvent was evaporated under reduced pressure, and the residue was purified by silica gel column chromatography to obtain 813 mg (94%) of glyoxal bishydrazone (I).

Melting point: 85°–87° C. $^1$H-NMR (DMSO-$d_6$): 7.31 (s, 2H), 6.57 (s, 4H) Mass (EI) m/e: 86 (M$^+$) IR (KBr) cm$^{-1}$: 3344, 3161, 1577, 1075, 919

EXAMPLE 1

Synthesis of 1-Amino-1,2,3-triazole (III)

In a reactor were charged 430 mg of glyoxal bishydrazone (I) obtained in Reference Example 1 and 5.0 ml of water, and the mixture was stirred at room temperature. To the mixture were added 58 mg of tungsten (VI) oxide and 0.5 ml of a 30% aqueous hydrogen peroxide solution, followed by stirring at that temperature for 12 hours. After completion of the reaction, any insoluble matter was removed by filtration, and the solvent was evaporated under reduced pressure to obtain 309 mg (yield: 74%) of 1-amino-1,2,3-triazole (III).

Boiling point: 124°–125° C./6 mmHg Melting point: 49°–50° C. $^1$H-NMR (DMSO-$d_6$): 7.89 (s, 1H), 7.64 (s, 1H), 7.00 (s, 2H) Mass (FAB$^+$) m/e: 85 (M$^+$+1)

EXAMPLE 2

Synthesis of 1-Amino-1,2,3-triazole (III)

In a reactor were charged 430 mg of glyoxal bishydrazone (I) obtained in Reference Example 1 and 5.0 ml of water, and the mixture was stirred at room temperature. To the mixture were added 72 mg of molybdenum (VI) oxide and 0.5 ml of a 30% aqueous hydrogen peroxide solution, followed by stirring at that temperature for 12 hours. After completion of the reaction, any insoluble matter was removed by filtration, and the solvent was evaporated under reduced pressure to give 294 mg (yield: 70%) of 1-amino-1,2,3-triazole (III).

The data of $^1$H-NMR (DMSO-$d_6$) and Mass (FAB$^+$) m/e, boiling point and melting point were the same as in Example 1.

EXAMPLE 3

Synthesis of 1-Amino-1,2,3-triazole (III)

In a reactor were charged 430 mg of glyoxal bishydrazone (I) obtained in Reference Example 1 and 5.0 ml of water, and the mixture was stirred at room temperature. To the mixture were added 40 mg of titanium (IV) oxide and 0.5 ml of a 30% aqueous hydrogen peroxide solution, followed by stirring at that temperature for 12 hours. After completion of the reaction, any insoluble matter was removed by filtration, and the solvent was evaporated under reduced pressure to obtain 235 mg (yield: 56%) of 1-amino-1,2,3-triazole (III).

The data of $^1$H-NMR (DMSO-$d_6$) and Mass (FAB$^+$) m/e, boiling point and melting point were the same as in Example 1.

EXAMPLE 4

Synthesis of 1-Amino-1,2,3-triazole (III)

In a reactor were charged 430 mg of glyoxal bishydrazone (I) obtained in Reference Example 1 and 5.0 ml of water, and the mixture was stirred at room temperature. To the mixture were added 40 mg of copper (II) oxide and 0.5 ml of a 30% aqueous hydrogen peroxide solution, followed by stirring at that temperature for 12 hours. After completion of the reaction, any insoluble matter was removed by filtration, and the solvent was evaporated under reduced pressure to give 193 mg (yield: 46%) of 1-amino-1,2,3-triazole (III).

The data of $^1$H-NMR (DMSO-$d_6$) and Mass (FAB$^+$) m/e, boiling point and melting point were the same as in Example 1.

EXAMPLE 5

Synthesis of 1-Amino-1,2,3-triazole (III)

In a reactor were charged 430 mg of glyoxal bishydrazone (I) obtained in Reference Example 1 and 5.0 ml of water, and the mixture was stirred at room temperature. To the mixture were added 80 mg of iron (III) oxide and 0.5 ml of a 30% aqueous hydrogen peroxide solution, followed by stirring at that temperature for 12 hours. After completion of the reaction, any insoluble matter was removed by filtration, and the solvent was evaporated under reduced pressure to give 244 mg (yield: 58%) of 1-amino-1,2,3-triazole (III).

The data of $^1$H-NMR (DMSO-$d_6$) and Mass (FAB$^+$) m/e, boiling point and melting point were the same as in Example 1.

EXAMPLE 6

Synthesis of 1-Amino-1,2,3-triazole (III)

In a reactor were charged 430 mg of glyoxal bishydrazone (I) obtained in Reference Example 1 and 5.0 ml of water, and the mixture was stirred at room temperature. To the mixture were added 86 mg of cerium (IV) oxide and 0.5 ml of a 30% aqueous hydrogen peroxide solution, followed by stirring at that temperature for 12 hours. After completion of the reaction, any insoluble matter was removed by filtration, and the solvent was evaporated under reduced pressure to obtain 265 mg (yield: 63%) of 1-amino-1,2,3-triazole (III).

The data of $^1$H-NMR (DMSO-$d_6$) and Mass (FAB$^+$) m/e, boiling point and melting point were the same as in Example 1.

EXAMPLE 7

Synthesis of 1-Amino-1,2,3-triazole (III)

In a reactor were charged 813 mg of glyoxal bishydrazone (I) obtained in Reference Example 1 and 1.0 ml of ethanol, and the mixture was stirred at room temperature. To the mixture was added 2.0 g of manganese dioxide for dry cells (a product of Tosoh Corp.; effective oxygen content: 91% or more; hereinafter the same), followed by stirring at the same temperature for 2 hours. Then, 1.0 g of manganese dioxide for dry cells was further added thereto, and the stirring was continued at that temperature for an additional period of 5 hours. After completion of the reaction, any insoluble matter was removed by filtration, and the solvent was evaporated under reduced pressure to give 720 mg (yield: 91%) of 1-amino-1,2,3-triazole (III).

The data of $^1$H-NMR (DMSO-$d_6$) and Mass (FAB$^+$) m/e, boiling point and melting point were the same as in Example 1.

EXAMPLE 8

Synthesis of 1-Amino-1,2,3-triazole (III)

In a reactor were charged 813 mg of glyoxal bishydrazone (I) obtained in Reference Example 1 and 1.0 ml of ethanol, and the mixture was stirred at room temperature. To the mixture was added 2.0 g of manganese dioxide for ferrite (a product of Tosoh Corp.; effective oxygen content; 94% or more; hereinafter the same), followed by stirring at the same temperature for 2 hours. Then, 0.5 g of manganese dioxide for ferrite was further added thereto, and the stirring was continued at that temperature for 5 hours. After completion of the reaction, any insoluble matter was removed by filtration, and the solvent was evaporated under reduced pressure to give 720 mg (yield: 91%) of 1-amino-1,2,3-triazole (III).

The data of $^1$H-NMR (DMSO-$d_6$) and Mass (FAB$^+$) m/e, boiling point and melting point were the same as in Example 1.

REFERENCE EXAMPLE 2

Synthesis of 1,2,3-Triazole Hydrochloride (VIII)

In a reactor were charged 710 mg of 1-amino-1,2,3-triazole (III) obtained in Example 1 and 7.0 ml of water, and 5.5 ml of 2N hydrochloric acid was added thereto under cooling with ice, followed by stirring. A solution of 1.16 g of sodium nitrite in 4.0 ml of water was slowly added thereto dropwise at the same temperature, followed by stirring at room temperature for 3 hours. After completion of the reaction, the solvent was evaporated under reduced pressure, and to the residue was added ethanol. The precipitated insoluble matter was removed by filtration, and the solvent was evaporated under reduced pressure to give 810 mg (yield: 91%) of 1,2,3-triazole hydrochloride (VIII).

Melting point: 126°–128° C. $^1$H-NMR (CDCl$_3$): 12.31 (brs, 2H), 7.86 (s, 2H)

REFERENCE EXAMPLE 3

Synthesis of 1,2,3-Triazole

To 800 mg of 1,2,3-triazole hydrochloride (VIII) obtained in Reference Example 2 was added 2.0 ml of a saturated aqueous solution of sodium hydrogencarbonate for neutralization. Ethanol was added thereto, followed by evaporation under reduced pressure to remove the solvent. To the residue was added ethanol, and any insoluble matter was removed by filtration. The filtrate was evaporated under reduced pressure to remove the solvent, and the residue was distilled under reduced pressure to give 300 mg (yield: 57%) of 1,2,3-triazole (IX).

Boiling point: 95°–97° C./20 mmHg $^1$H-NMR (CDCl$_3$): 15.15 (brs, 1H), 7.86 (s, 2H)

EXAMPLE 9

Serial Synthesis of 1,2,3-Triazole (IX) from Glyoxal (VI)

In a reactor were charged a 40% aqueous solution of 5.80 g of glyoxal (VI), 4.00 g of hydrazine monohydrate, and 40 ml of water, and the mixture was stirred at room temperature for 30 minutes and than at 100° C. for 3 hours. After allowing the reaction mixture to cool, 93 mg of tungsten oxide and 6.0 ml of a 30% aqueous hydrogen peroxide solution were added thereto, followed by stirring at room temperature for 10 hours. The reaction mixture was filtered using Celite to remove any insoluble matter. To the filtrate (a solution containing 1-amino-1,2,3-triazole) was added 20 ml of 6N hydrochloric acid under ice-cooling, followed by stirring. A solution of 5.52 g of sodium nitrite in 15.0 ml of water was slowly added thereto dropwise at the same temperature, followed by stirring at room temperature for 2 hours. After completion of the reaction, the reaction mixture was rendered alkaline by addition of 3.50 g of potassium carbonate, and ammonium sulfate was added thereto to prepare a saturated solution. The resulting solution was extracted with ethyl acetate, and the extract was dried over anhydrous magnesium sulfate. The solvent was removed by evaporation under reduced pressure, and the residue was distilled under reduced pressure to give 1.52 g (55%) of 1,2,3-triazole (IX).

Boiling point: 95°–97° C./20 mmHg $^1$H-NMR (CDCl$_3$): 15.15 (brs, 1H), 7.86 (s, 2H)

Industrial Applicability

The process according to the present invention for preparing 1-amino-1,2,3-triazole (III) which is an important intermediate for synthesizing 1,2,3-triazole (IX), which is useful as a starting material of antibiotics, does not use a large quantity of an expensive or highly toxic reagent as required in conventional techniques. Therefore, the present invention makes it possible to prepare 1-amino-1,2,3-triazole at low cost without involving the problem of waste water disposal and thus brings about great industrial advantages.

We claim:

1. A process for preparing 1-amino-1,2,3-triazole represented by formula (III):

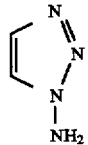

(III)

comprising cyclizing glyoxal bishydrazone represented by formula (I):

by reaction with an aqueous hydrogen peroxide solution in the presence of a catalytic amount of a transition metal oxide represented by formula (II):

(II)

wherein M represents a transition metal atom; and m and n, which may be the same or different, each represent an integer of 1 to 5.

2. A process as claimed in claim 1, wherein said transition metal atom is tungsten, titanium, molybdenum, copper, iron, or cerium.

3. A process as claimed in claim 1, which comprises cyclizing said glyoxal bishydrazone represented by formula (I) by reaction with manganese dioxide.

4. A process as claimed in claim 3, wherein said manganese dioxide is activated manganese dioxide.

5. A process as claimed in claim 3, wherein said manganese dioxide is manganese dioxide for dry cells or manganese dioxide for ferrite.

* * * * *